United States Patent [19]
Gardeski et al.

[11] Patent Number: 6,146,338
[45] Date of Patent: Nov. 14, 2000

[54] APPARATUS FOR DEFLECTING A CATHETER OR LEAD

[75] Inventors: Kenneth C. Gardeski, Plymouth; Corinne A. G. Poor, Roseville; David Lipson, Shoreview, all of Minn.

[73] Assignee: Medtronic, Inc., Minneapolis, Minn.

[21] Appl. No.: 09/298,605

[22] Filed: Apr. 23, 1999

[51] Int. Cl.$^7$ .................................................... A61B 5/00
[52] U.S. Cl. ............................................................ 600/585
[58] Field of Search ................................. 600/433–435, 600/585

[56] References Cited

U.S. PATENT DOCUMENTS

| | | |
|---|---|---|
| 4,033,357 | 7/1977 | Helland et al. . |
| 4,136,703 | 1/1979 | Wittkampf . |
| 4,488,561 | 12/1984 | Doring . |
| 4,506,680 | 3/1985 | Stokes . |
| 4,572,605 | 2/1986 | Hess . |
| 4,676,249 | 6/1987 | Arenas et al. . |
| 4,727,877 | 3/1988 | Kallok . |
| 4,815,478 | 3/1989 | Buchbinder et al. . |
| 4,922,607 | 5/1990 | Doan et al. . |
| 4,940,062 | 7/1990 | Hampton et al. . |
| 5,040,543 | 8/1991 | Badera et al. . |
| 5,115,818 | 5/1992 | Holleman et al. . |
| 5,170,787 | 12/1992 | Lindegren et al. . |
| 5,282,844 | 2/1994 | Stokes et al. . |
| 5,327,906 | 7/1994 | Fideler . |
| 5,473,812 | 12/1995 | Morris et al. . |
| 5,662,119 | 9/1997 | Brennen et al. . |
| 5,728,148 | 3/1998 | Bostrom et al. . |
| 5,728,149 | 3/1998 | Laske et al. . |

OTHER PUBLICATIONS

Introduction to Physical Metallurgy, 2d Ed., by Auer, 1974, pp. 374–375.
Custom 450 alloys available from Carpenter Technology Corp, Reading PA—data sheets, Jul. 1993.
Custom 455 alloys available from Carpenter Technology Corp, Reading PA—data sheets, Sep. 1986.

*Primary Examiner*—Max Hindenburg
*Attorney, Agent, or Firm*—Reed A. Duthler; Harold R. Patton

[57] ABSTRACT

A deflectable stylet or guidewire formed of an elongated tube having a coil mounted to its distal end and a movable tension or push wire mounted within the coil and the tube, mechanically coupled to the distal end of the coil. A backbone is located within the coil, mechanically coupled to the proximal and distal ends of the coil and extending along one side of the coil. The backbone may be provided with projections extending laterally between adjacent turns of the coil and may have a generally arcuate cross section having a width greater than its arc height. In some embodiments the backbone may be formed from a tube having a slot extending longitudinally along one side thereof. In some embodiments the backbone may be attached to the coil at points between the proximal and distal ends of the coil.

4 Claims, 5 Drawing Sheets

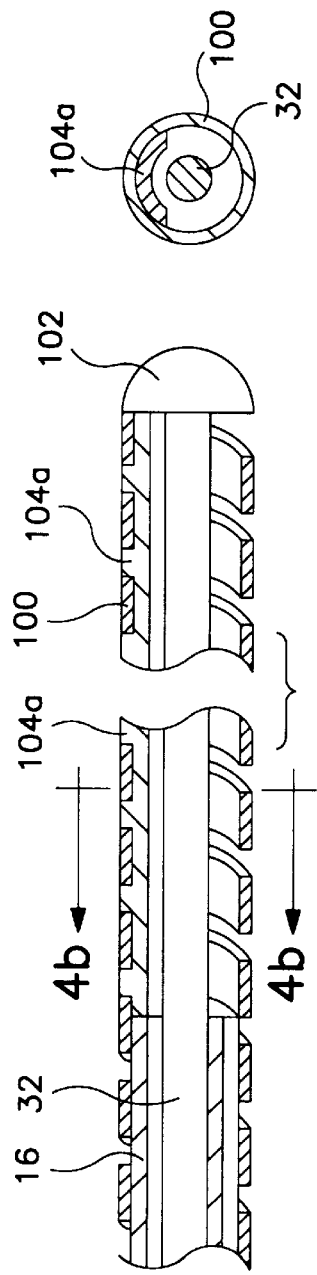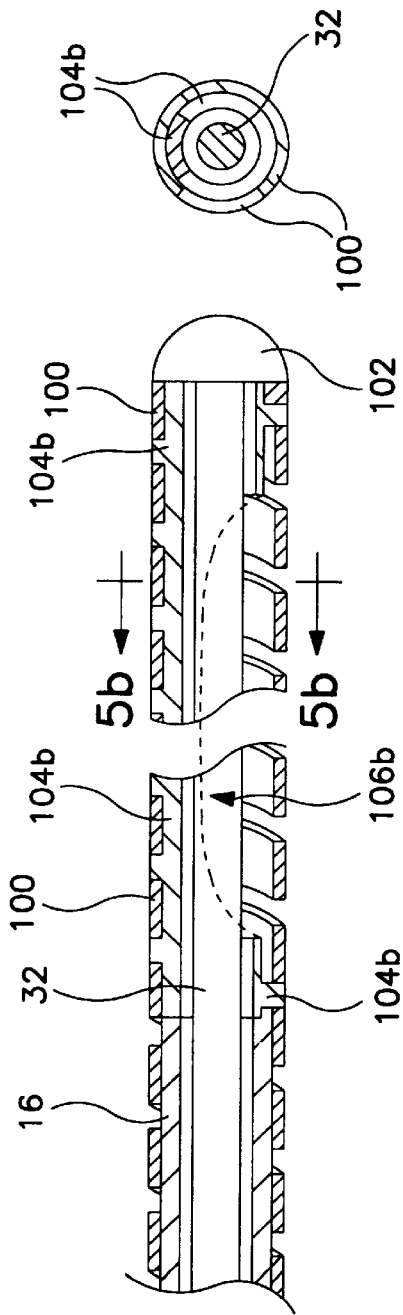

APPARATUS FOR DEFLECTING A CATHETER OR LEAD

BACKGROUND OF THE INVENTION

The present invention relates generally to implantable leads and catheters and more particularly to mechanisms for deflecting implantable leads and catheters to assist in guiding them through the vascular system.

Over the years, quite a number of mechanisms have been disclosed and employed to deflect catheters and implantable leads. These have taken the form of deflectable guidewires and deflectable stylets, typically operable from the proximal end of the lead or catheter, which controllably impart a curve to the distal portion of the lead or catheter. One group of devices comprise deflectable stylets or guidewires which employ a straight, tubular outer member with a curved inner member, the inner and outer members movable relative to one another. Examples of this type of deflection mechanism are disclosed in U.S. Pat. No. 4,136,703 issued to Wittkampf and U.S. Pat. No. 5,728,148 issued to Bostrom et al. Alternatively, deflection devices employing a curved outer member and a relatively straight inner member are also known to the art, as disclosed in U.S. Pat. No. 4,676,249 issued to Arenas and U.S. Pat. No. 5,040,543 issued to Badera et al. In devices of both types, the relative position of the inner member with respect to the outer member determines the degree to which the curved member (inner or outer) is allowed to display its preset curvature.

A more commonly employed approach to providing controllable deflection employs a generally straight outer member and a tension or push wire located within the outer member which on advancement or retraction causes the outer member to bend. Examples of such deflection mechanisms can be found in U.S. Pat. No. 4,815,478 issued to Buchbinder et al., and U.S. Pat. No. 4,940,062 issued to Hampton et al.

Particularly in the context of deflectable stylets intended for use in conjunction with implantable medical leads such as pacing and cardioversion leads, steerable stylets employing this third type of deflection mechanism are disclosed in U.S. Pat. No. 5,662,119 issued to Brennen et al., U.S. Pat. No. 5,170,787 issued to Lindegren, and U.S. Pat. No. 5,327,906 issued to Fideler et al, all of which are incorporated herein by reference in their entireties.

While all of the mechanisms disclosed in the above cited prior art patents are at least to some degree workable, there is still a perceived need for a deflectable stylet or guidewire which has the capability to impart a controllable, relatively small radius curvature to the distal end of a cardiac pacing lead or catheter and which is sufficiently durable to allow for repeated use.

SUMMARY OF THE INVENTION

The present invention includes a variety of embodiments of deflectable stylets or guidewires all including an elongated tubular portion which may be fabricated of nitinol, stainless steel or other appropriate metal and which may take the form, for example, of a length of hypodermic tubing, preferably stainless steel, super-precision drawn, smooth-bore tubing. Located at the distal end of the tubing is a deflectable tip portion which in turn includes a coil, coupled to the distal tip of the tube, preferably fabricated of wire which is rectangular in cross-section and wound into a flat-wound coil such that the width of the wire is greater than the thickness of the wire measured radially. A longitudinally movable internal tension or push wire is located within the tube and extends through the coil to the distal end of the coil where it is mechanically coupled to the distal end of the coil. Also provided is a backbone member which may take one of several forms and which is configured to prevent longitudinal compression and/or expansion of the coil along one side thereof so that longitudinal movement of the wire within the tube and coil causes deflection of the coil. The coiled wire, tension/push wire and the backbone may be fabricated of stainless steel, nitinol, or other appropriate material. In particular, the coil and backbone are preferably formed of a wrought stainless steel, more preferably a precipitation hardened stainless steel such as PH15-7 Mo or 17-7PH or similar alloys which, in their annealed condition are readily weldable and which may be shaped by precision stamping and coiling. The backbone member is also preferably configured to prevent out of plane twisting of the coil as a result of longitudinal movement of the internal wire, and more preferably is configured to provide a smooth and even bend by preventing relative movement of individual turns of the coil relative to one another, along one side of the coil.

In a first embodiment, the backbone takes the form of an elongated member provided with laterally extending projections which are sized to fit between adjacent turns of the coil along one side of the coil allowing compression or expansion of the coil only along the opposite side of the coil in response to longitudinal movement of the internal wire. The projections of the backbone also prevent relative longitudinal movement of individual turns of the coil along the side of the coil engaging the backbone, providing a smooth, continuous bend. The backbone is preferably coupled to the coil at its tip and may optionally be welded to the coil along its length, at some or all of the points at which the projections of the backbone contact individual turns of the coil. In this embodiment, the backbone preferably has a generally arcuate configuration in cross section, and has a width substantially greater than its arc height in order to provide a preferred bending axis and prevent out of plane twisting of the deflectable portion of the stylet or guidewire during longitudinal movement of the internal wire.

In a second embodiment, the backbone takes the form of a tube having external threads formed thereon which correspond to the spaces between the turns of the coil. In this embodiment, the tube is provided with a longitudinal slot or recess such that over a portion of the length of the tube, the tube engages the coil only along one side thereof, allowing compression or expansion of the coil only along the opposite side of the coil in response to longitudinal movement of the internal wire. In this embodiment, the backbone also has a generally arcuate configuration in cross section along the length of the slot, and along this length also has a width substantially greater than its arc height in order to provide a preferred bending axis and prevent out of plane twisting of the deflectable portion of the stylet or guidewire during longitudinal movement of the internal wire. The backbone is preferably coupled to the coil at its tip and may optionally be welded to the coil along its length, at the points at which the projections of the backbone contact individual turns of the coil.

A third embodiment of the invention employs a backbone taking the form of an elongated member having a generally arcuate configuration in cross section, but which does not include projections as set forth in conjunction with the first and second described embodiments. The backbone is instead welded to the coil at one or more locations between its proximal and distal end to prevent relative movement of the individual coils.

A final alternative embodiment to the present invention integrates the backbone with the coil itself. In this case, the coil is formed of a material such as the PH15-7 Mo or 17-7PH stainless steels referred to above which in a ductile (annealed) condition allows portions of the turns along one side of the coil to be compressed, in turn causing the material of the coil to form a projection which engages the next successive turn of the coil. The projections so formed may simply contact the next portion of the coil in which case the internal wire may only be used as a tension or pull wire, the individual projections extending from turns of the coil serving only to prevent relative movement of the individual turns of the coil toward one another. However, the tabs or projections so formed may alternatively be welded to the next successive coil member, also preventing relative movement of individual ones of the coils apart from one another, along the side of the coil in which the tabs or projections are formed. In this embodiment, it is preferable that the tabs or projections are formed such that their base width is greater than the arc height of the section of the coil across which the tabs extend, in order to provide increased resistance to out of plane twisting of the coil during longitudinal movement of the internal wire.

In all embodiments in which wrought stainless steels as discussed above or similar materials are employed for the coil and backbone, the coil and backbone are preferably fabricated from the metal in its annealed, relatively softer ductile condition, allowing winding of the coil without substantial spring-back and facilitating any required stamping or forming operations performed on the coil or backbone. The coil and backbone are then preferably welded to one another. Following assembly of the coil and backbone assembly and any welding of the components to one another, the assembly is preferably heat treated and stress relieved to temper the assembly and produce a desired final set of mechanical embodiments, properties (hardness, spring constant, tensile strength, etc.). In some the tubing making up the majority of the stylet body may also be formed of such alloys and welded to the coil and core, preferably prior to heat treatment.

FIF. 4a is a side, sectional view through a first embodiment of a deflectable stylet according to the present invention.

FIG. 4b is a cross sectional view through the stylet of FIG. 4a.

FIG. 5a is a side, sectional view through a second embodiment of a deflectable stylet according to the present invention.

FIG. 5b is a cross sectional view through the stylet of FIG. 5a.

Figure 6A:
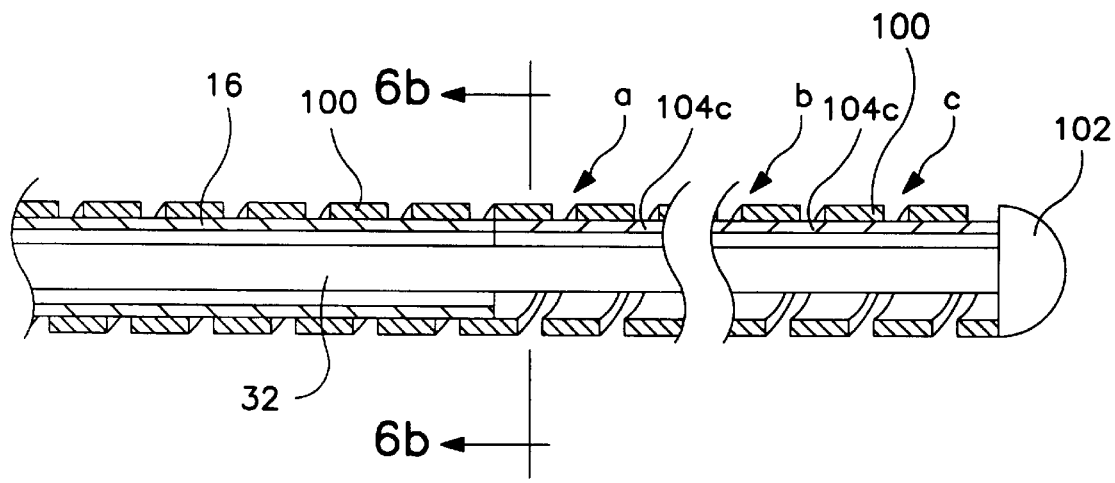

FIG. 6a is a side, sectional view through a third embodiment of a deflectable stylet according to the present invention.

Figure 6B:
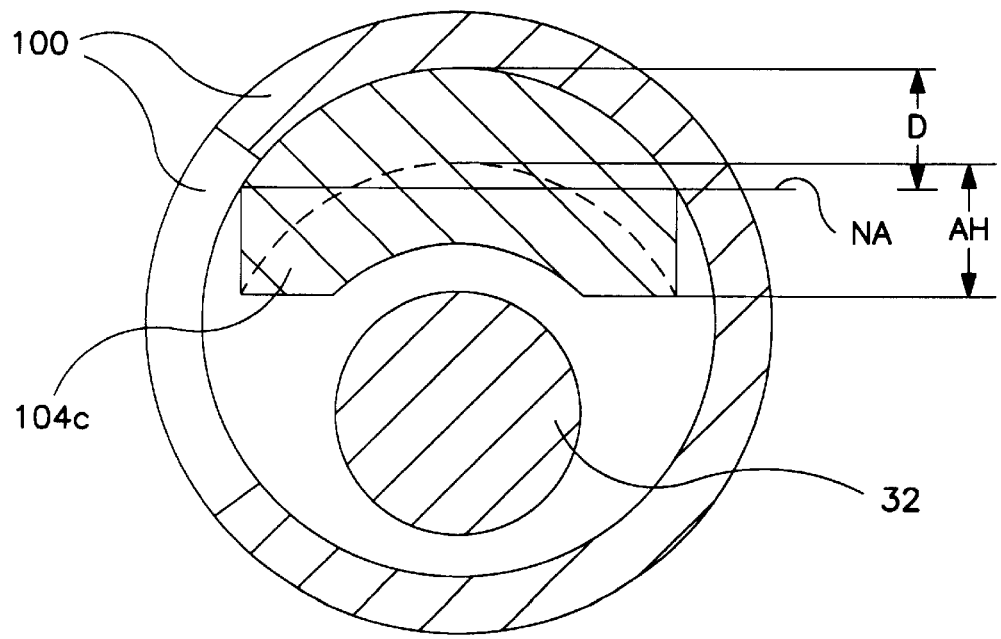

FIG. 6b is a cross sectional view through the stylet of FIG. 6a.

Figure 7A:
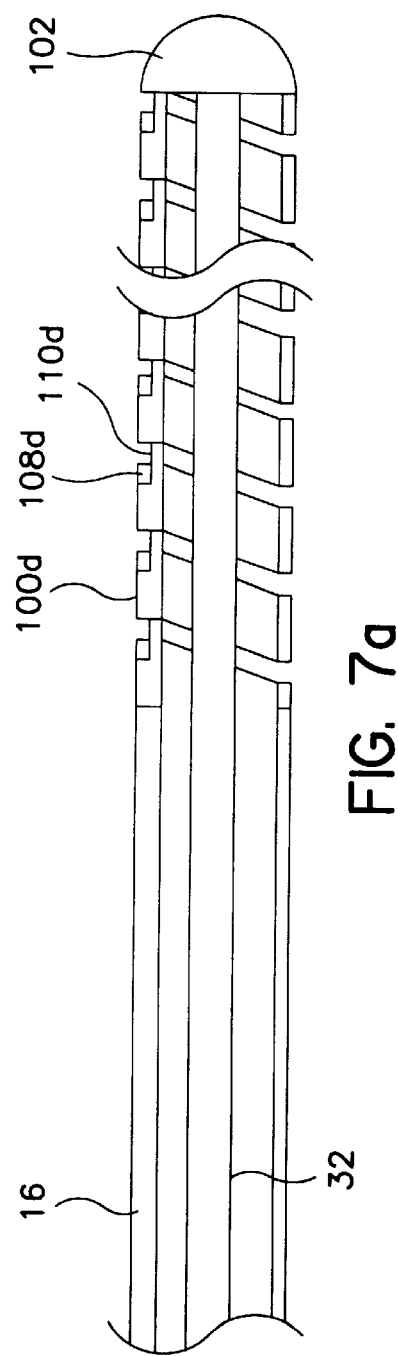

FIG. 7a is a sectional view through a fourth embodiment of a deflectable stylet according to the present invention.

Figure 7B:
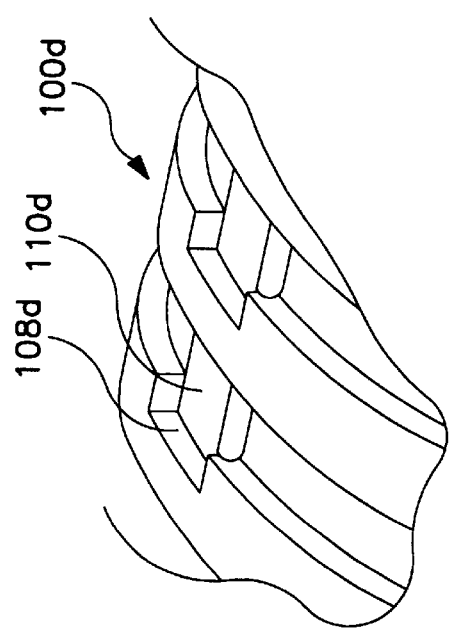

FIG. 7b is a perspective view of a portion of the deflectable stylet of FIG. 7a.

DETAILED DESCRIPTION OF THE PREFERRED EMBODIMENTS

Figure 1:
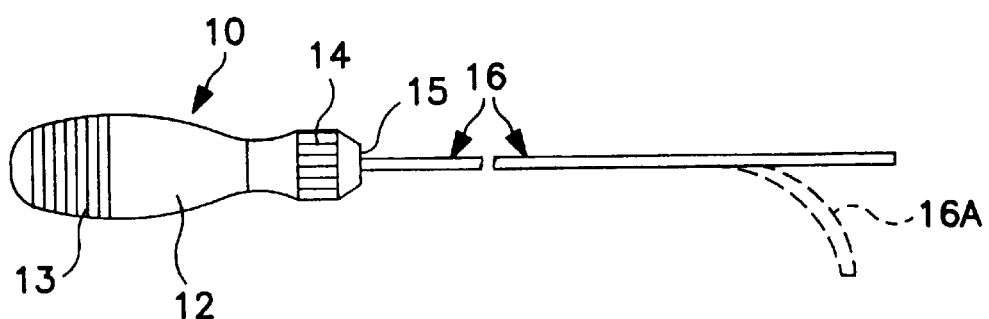
FIG. 1 is a plan view of a deflectable stylet according to the present invention.

FIG. 1 illustrates a plan view of a deflectable stylet according to the present invention. The deflectable stylet 16 is provided with a handle 10 which includes a main handle portion 12 and a spinner or knob portion 14, mounted rotatably with respect to the primary handle portion 12. The deflectable stylet 16 exits from a proximal recess 15, within spinner or knob 14. The rotation of spinner or knob 14 or distal advancement of knob 14 relative to the handle 12 causes deflection of the distal portion of stylet 16 to a curved configuration as illustrated at 16A.

Deflectable stylet 16 employs an outer tubular member and an inner tension wire which, when it applies tension to the distal tip of deflectable stylet 16, causes the tip of the stylet to curve as described below in conjunction with FIG. 3.

Figure 2:
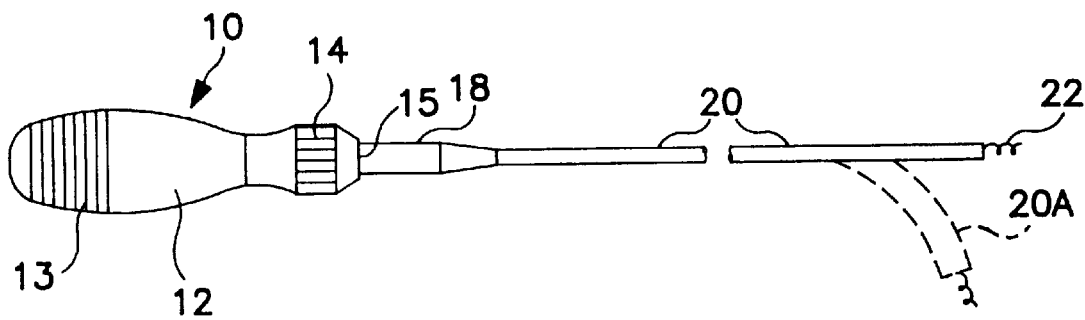
FIG. 2 is a plan view of the deflectable stylet of FIG. 1 shown inserted into an implantable cardiac pacing lead.

FIG. 2 is a plan view of the deflectable stylet of FIG. 1 inserted into a cardiac pacing lead 20. Cardiac pacing lead 20 is provided with a connector assembly 18 located at its proximal end, which typically carries a connector pin as is typical of cardiac pacing leads. For example, the distal portion of the connector assembly 18 may correspond to the IS-1 connector standard as disclosed in U.S. Pat. No. 4,922, 607 issued to Doan et al., also incorporated herein by reference in its entirety. However, other connector configurations, such as disclosed in U.S. Pat. No. 4,488,561 issued to Doring or U.S. Pat. No. 4,572,605 issued to Hess et al., both also incorporated herein by reference in their entireties, may also be employed. At the distal end of pacing lead 20 is located a fixed helical electrode 22, such as that disclosed in U.S. Pat. No. 5,473,812 issued to Morris et al. and incorporated herein by reference in its entirety, which is screwed into heart tissue in order to stimulate the heart. However, any other type of known pacing electrode may be substituted for electrode 22, or alternatively other types of electrodes such as cardioversion or defibrillation electrodes may be added to or substituted for electrode 22. Examples of pacing and cardioversion electrodes generally that might be employed in conjunction with a lead to be deflected by the deflectable stylet of the present invention include those described in U.S. Pat. No. 5,282,844 issued to Stokes et al., U.S. Pat. No. 4,506,680 issued to Stokes, U.S. Pat. No. 4,033,357 issued to Helland et al., U.S. Pat. No. 4,727,877 issued to Kallok, U.S. Pat. No. 5,115,818 issued to Holleman et al. and U.S. Pat. No. 5,728,149 issued to Laske et al., all also incorporated herein by reference in their entireties.

As illustrated, the connector assembly 18 of the lead 20 is inserted into the distal facing opening 15 within spinner or knob 14. The spinner or knob 14 is free to rotate and slide with respect to connector assembly 18. The internal slider member (not visible in this view) located within handle 10 may either frictionally engage the connector pin of the connector assembly 18, or may be free to rotate with respect to the connector pin. For example, in the context of a device employing a fixed helical electrode, rotation of the entire lead with respect to the deflectable stylet would be required in order to screw the helical electrode 22 into heart tissue. However, in the context of a lead employing a tined electrode or employing other electrodes not requiring rotation of the lead body to accomplish fixation, the inner slider member of the handle 10 might frictionally engage the connector pin of connector assembly 18, further facilitating the steering of the lead through the vascular system to the desired location within the heart.

Figure 3:
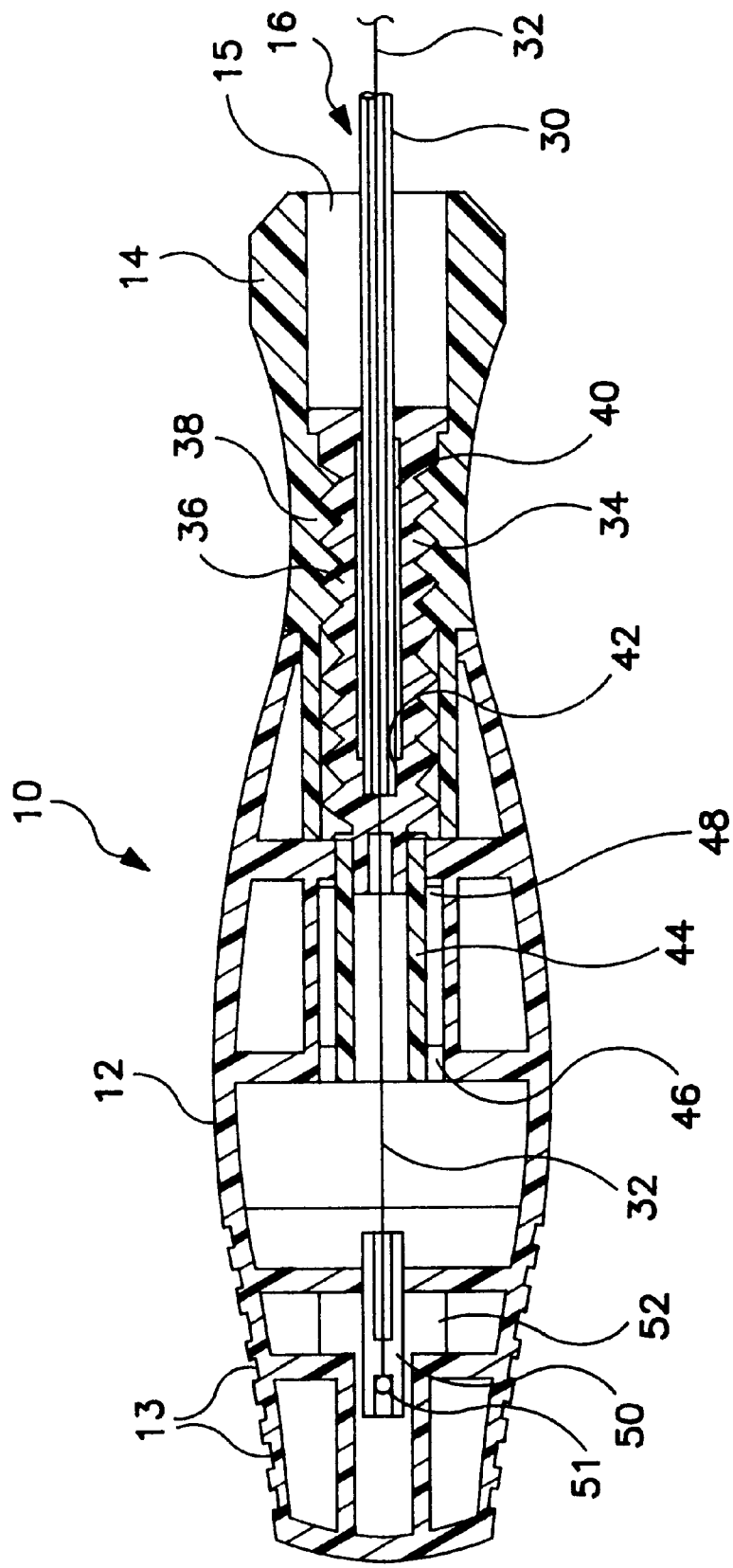
FIG. 3 is a sectional view through an exemplary handle for use with a deflectable stylet according to the present invention.

FIG. 3 illustrates a sectional view through the handle 10 of the deflectable stylet illustrated in FIG. 1. The handle comprises a main handle portion 12 and a spinner or knob portion 14, both of which may be molded plastic parts. Spinner 14 is provided with inwardly facing screw threads 38 which engage with correspondingly outwardly facing screw threads 36 on the inner slider member 34. Fixedly coupled to the proximal end of slider 34 is a cylindrical extension 44 which is provided with two oppositely arranged outwardly projecting tabs 46 which engage with corresponding longitudinal grooves 48 formed in the major handle portion 12. Slider 34 and extension 44 may also be molded plastic parts. Interaction of the outwardly extending tabs 46 and the grooves 48 prevent rotation of tubular extension 44 and of slider member 34 relative to the major handle portion 12. As such, rotation of knob or spinner 14 relative to the major handle portion 12 causes proximal or distal movement of slider member 34 and extension 44 relative to both the major handle portion 12 and the knob or spinner 14.

The deflectable stylet is arranged such that the outer tubular member 30 of the stylet, which may be formed of stainless steel or nitinol tubing is fixedly mounted within the proximal portion 42 of the inner lumen 40 of slider 34, while the tension wire 32 extends through slider 34 to an anchoring mechanism which comprises a threaded rod 50 and an associated adjuster nut 52, located within the major handle portion 12. The threaded rod 50 is provided with a lumen through which tension wire 36 passes, and is arranged such that a ball 51 or other expanded diameter portion located at the proximal end of tension wire 32 anchors the wire with respect to threaded rod 50. Threaded rod 50 and nut 52 are both mounted rotationally fixed with respect to major handle portion 12, with adjuster nut 50 employed to position tension wire 32 so that in the circumstance in which the internal slider 34 is located at its most proximal position (as illustrated), no tension is applied to the distal tip of the outer tubular member 30 of the deflectable stylet 16, so that the deflectable stylet 16 displays a straight configuration. On rotation of spinner or knob 14 to advance inner slider member 34 with respect to the major handle portion 12, the outer tubular portion 30 of the deflectable stylet is also advanced with respect to tension wire 32, causing tension wire 32 to apply tension to the distal tip of the tubular member 30, correspondingly causing deflection of the tubular member.

Opening 15 in the distal portion of the knob or spinner 14 is sized to accept the connector assembly of the lead with which the deflectable stylet is intended to be used, with sufficient clearance, so that rotation of knob or spinner 14 does not cause corresponding rotation of the connector assembly. The internal lumen 40 of the inner slider member 34 may be sized either to frictionally engage a connector pin at the proximal end of the lead connector assembly, or may be sized to be slightly greater than the connector pin of the associated lead. If the opening 40 is sized to be somewhat greater than the outer diameter of the connector pin, then the entire lead may be rotated with respect to the deflectable stylet. This is particularly desirable in the context of a lead as illustrated in FIG. 1 which employs a fixation helix 22 (FIG. 2), fixedly mounted to the distal end of the lead body, as it allows the lead to be screwed into the tissue, around the stylet, in its deflected configuration. As noted above, however, as noted in the case of a lead employing a tined electrode or other fixation mechanism, it may be desirable to size the internal lumen 40 so that it frictionally engages a connector pin on the lead.

FIG. 4a is a sectional view through the distal portion of a first embodiment of a deflectable stylet or guidewire according to the present invention. In this view, the tubular member 16 which comprises the major length of the deflectable stylet or guidewire may be formed of nitinol or stainless steel and may take the form of a length of hypodermic tubing as described above. The internal wire 32 if used in conjunction with a handle as illustrated in FIGS. 1–3 serves as a tension wire, and during deflection is pulled proximally relative to the tubular member 30. However, in alternative embodiments, the wire 32 may serve as a push wire, and may be moved distally relative to tubular member 30 to cause deflection of the stylet or guidewire. The stylet is provided with a coil 100, welded, soldered or adhesively bonded to the distal end of tubular member 30. A backbone 104a is provided having a generally arcuate configuration in cross section and, in cross-section, having a width which is greater than its arc height, as discussed above. The backbone is welded or soldered or adhesively bonded to the distal end of the tubular member 30 and/or proximal end of coil 100 and extends alongside coil 100 to the tip member 102. The backbone 104a is provided with regular extending projections or tabs which are sized to fit between adjacent turns of coil 100, preventing their relative longitudinal movement, along the side of the coil in which the backbone is located. The distal tip of the guidewire takes the form of a rounded tip member 102 which is preferably soldered or welded to wire 32, the distal end of coil 100 and the backbone 104a. In some embodiments, the individual turns of the coil 100 intermediate its proximal and distal ends may be soldered or welded to the adjacent tabs or projections of the backbone 104a to provide for a structure with greater torsional rigidity. Because the backbone is provided with projections which prevent longitudinal movement of individual turns of the coil relative to one another during deflection, the resulting curvature produced displays a smooth, readily controllable curvature along its length during deflection. The projections on the backbone also make it substantially easier to weld the backbone to the coil at one or more locations along their lengths.

In a preferred embodiment according to FIG. 4a, and according to FIGS. 5a, 6a and 7a discussed below, the coil and backbone are fabricated of a wrought stainless steel such as semi-austenitic precipitation hardening PH15-7 Mo or 17-7PH alloys which in their solution-annealed condition have a hardness of about $R_B$ 85–88 on the Rockwell hardness scale or of an alloy having similar properties such as the Custom 450 or Custom 455 alloys available from Carpenter Technology Corp, Reading Pa. The backbone is stamped or coined to produce the configuration illustrated while the alloy is in its fully annealed state. The coil and backbone are then welded to one another, preferably at both their proximal and distal ends and more preferably at points along their length where the projections of the backbone are adjacent turns of the coil. The assembly is then heat treated and stress relieved to provide a spring temper and an accompanying increase in hardness and tensile strength. In particular, the PH15-7 Mo and 17-7PH alloys may be heat treated to produce the RH 950 F condition according using the process described in Introduction to Physical Metallurgy, 2d Ed., by Auer, 1974, pages 374–375 incorporated herein by reference in its entirety. The Custom 450 and Custom 455 alloys may be heat treated to produce the H 1000 condition according using the process described in the Alloy Data sheets for the Custom 450 and Custom 455 alloys, published by Carpenter Technology Corp. in 1986 and 1993, respectively, both also incorporated herein by reference in their entireties. An additional alternative material which may be useful in practicing the present invention is BETA-C™ alloy, a titanium based alloy produced by RMI Titanium Company, Niles, Ohio. Particularly in embodiments in which the size of the deflectable stylet is small enough to fit within the lumen of a coiled conductor of a pacing lead, , e.g. about 0.010 inches in diameter or less, this fabrication process substantially simplifies the production of the required small diameter coil and stamped backbone and eases the welding process, while allowing an assembly which ultimately has the hardness, tensile strength and spring properties required to produce a workable and durable device.

In some embodiments of the present invention, tube 16 may also be made of the same type of alloy as the preferred alloys for the coil and backbone as discussed above. In such embodiments, the coil and/or backbone may be welded to the tube and the assembly subsequently heat treated as discussed above. Alternatively, the tube 16 could be heat treated prior to welding or other form of attachment to the coil and backbone.

FIG. 4b shows the deflectable stylet or guidewire of FIG. 4a in cross-section. In this view, it can be seen that the backbone 104a in cross-section has a width which is greater than its arc height between the projections or tabs. Whether or not the backbone is welded to the coil, this configuration assists in maintaining torsional rigidity and in preventing out of plane twisting of the stylet or guidewire during deflection.

FIG. 5a shows a side sectional view through a second embodiment of a deflectable stylet or guidewire according to the present invention. In this view, the tubular member 30, the wire 32, the coil 100 and the tip member 102 may correspond to the tubular member 30, wire 32, and tip 102 of the stylet or guidewire in FIG. 4a. The backbone 104b, however, differs from the backbone 104a of FIG. 4a in that its formed as a tube having a longitudinal slot or recess 106b extending along the deflectable portion of the stylet or guidewire. The recess allows relative longitudinal movement and expansion and compression of the coil along the side of the tube which is adjacent the slot or recess 106b, but prevents elongation or compression of the side of the coil 100 on the side of the tube opposite the slot. As illustrated, the backbone 104b is fabricated of a tube which is provided with external threading which corresponds to the spaces between individual turns of coil 104b and which, along the side of the tube opposite the recess or slot 106b functions in a manner analogous to the backbone 104a described in conjunction with FIG. 104a. The backbone 104b is preferably soldered or welded to the distal end of the tubular member 30 and/or the proximal end of coil 100, as well as being correspondingly connected to the tip member 102 and the distal end of coil 100. As in the case of the embodiment illustrated in FIG. 104a, the individual threads of the backbone 104b extending between adjacent turns of the coil 100 may optionally be welded to adjacent turns of the coil 100 intermediate its proximal and distal ends to provide for increased torsional rigidity.

FIG. 5b illustrates a cross-sectional view through the guidewire or stylet of FIG. 5a. In this view it can be seen that the portion of the backbone opposite the elongated slot or aperture 106b has a generally arcuate cross section which has a width which is greater than its arc height, in portions of the backbone between the radially extending threads.

FIG. 6a illustrates a third embodiment of a stylet or guidewire according to the present invention. In this embodiment, the tubular member 30, the internal wire 32, the tip 102 and the coil 100 may correspond to identically numbered elements in FIGS. 4a and 5a. In this embodiment, the backbone 104c also takes the form of an elongated member as in FIG. 4a. However, unlike the backbone 104a of FIG. 4a, the backbone 104c is not provided with radially extending threads to extend intermediate adjacent turns of the coil 100. The backbone 104c is preferably soldered or welded to the distal end of the tubular member 30 and/or the proximal end of coil 100, as well as being correspondingly connected to the tip member 102 and the distal end of coil 100. In this embodiment, one or more of the individual turns of the coil 100 intermediate its proximal and distal ends may be welded or soldered to adjacent portions of the backbone 104c, to prevent relative longitudinal movement of the turns of the coil relative to one another along backbone 104c. For example, every other turn of the coil may be welded to the backbone, for example at locations A, B and C as illustrated.

FIG. 6b illustrates a cross-section through the deflectable portion of the stylet or guidewire illustrated in FIG. 6a and illustrates that the width of the cross-section of the backbone 104c is greater than its arch height, in order to provide for enhanced torsional rigidity and resistance to out of plane twisting of the deflectable portion of the guidewire or stylet during longitudinal movement of wire 32. As illustrated, the cross section of the backbone according to this embodiment, as in the embodiments discussed above, defines a preferred axis of bending or neutral axis NA. preferably, the distance D from the neutral axis NA to the outer circumference of the is minimized to the extent possible, to reduce bending stress. As illustrated, the width of the backbone in cross section is preferably at least twice the arc height AH (the height of the arc defined by the center-line of the cross section, as illustrated). In the particular embodiment illustrated, the width of the backbone is approximately four times the arc height.

FIG. 7a illustrates a fourth embodiment of a deflectable guidewire or stylet according to the present invention. In this embodiment, tube 30, wire 32 and tip 102 may correspond to those illustrated in FIGS. 4–6 above. In this embodiment, however, the coil 100d is modified by localized deformation, and in particular by compression to form recesses 108d in adjacent turns of the coil along one side thereof, in turn causing extrusion of material to provide for longitudinally extending projections 110d. In this embodiment, the coil 100d should be formed of a relatively soft material, such as a PH17-5 Mo or 17-7PH stainless steel which may be formed to display the desired configuration and thereafter heat treated in order to harden the coil. In this embodiment, the individual projections 110d on each turn of the coil 100d may simply abut the next successive coil, if the wire 32 is employed as a tension wire. Projections 100d in this embodiment would prevent relative movement of the individual turns of the coil toward one another along the side of the coil on which the projections 110d are formed. In an alternative embodiment, the projections 110d may each be welded or soldered to the next adjacent turn of the coil 110d. In this embodiment, longitudinal movement of the individual turns apart from one another would be prevented so that the wire 32 might alternatively function as a push wire, causing deflection of the tip of the guidewire or stylet due to longitudinal movement of the wire 32 distally. Welding the tabs 110d of each turn of the coil 100d to the next successive coil also provides a structure with increased torsional rigidify, resistant to out of plane twisting during deflection caused by longitudinal movement of wire 32. Preferably, the projections 110d have a width measured circumferentially which is greater than the arc height of the coil in the section across which the projections extend, in order to provide for increased torsional rigidity.

FIG. 7b is a perspective view of portions of adjacent turns of the coil 100d, illustrating the configuration of the recesses 108d and the projections 110d.

What is claimed is:

1. A deflectable stylet or guidewire, comprising:

an elongated tubular member having proximal and distal ends;

a coil having proximal and distal ends and mounted to the distal end of the tubular member;

a longitudinally movable wire mounted within the coil and tubular member, mechanically coupled to the distal end of the coil; and a backbone located within the coil, mechanically coupled to the proximal and distal ends of the coil, extending along one side of the coil and provided with projections extending laterally between adjacent turns of the coil.

2. A deflectable stylet or guidewire, comprising:

an elongated tubular member having proximal and distal ends;

a coil having proximal and distal ends and mounted to the distal end of the tubular member;

a longitudinally movable wire mounted within the coil and tubular member, mechanically coupled to the distal end of the coil; and a backbone located within the coil, extending along one side of the coil and mechanically coupled to the proximal and distal ends of the coil, the backbone having a generally arcuate cross section having a width greater than its arc height.

3. A stylet or guidewire according to claim 2 wherein the backbone is provided with projections extending laterally between adjacent turns of the coil.

4. A stylet or guidewire according to any of claims 2 to 3 wherein the backbone is mechanically coupled to individual turns of the coil intermediate the proximal and distal ends of the coil.

* * * * *